US 6,652,514 B2

(12) United States Patent
Ellman et al.

(10) Patent No.: US 6,652,514 B2
(45) Date of Patent: Nov. 25, 2003

(54) INTELLIGENT SELECTION SYSTEM FOR ELECTROSURGICAL INSTRUMENT

(76) Inventors: Alan G. Ellman, 1135 Railroad Ave., Hewlett, NY (US) 11557; Jon C. Garito, 1135 Railroad Ave., Hewlett, NY (US) 11557

( * ) Notice: Subject to any disclaimer, the term of this patent is extended or adjusted under 35 U.S.C. 154(b) by 20 days.

(21) Appl. No.: 09/950,611

(22) Filed: Sep. 13, 2001

(65) Prior Publication Data

US 2003/0050633 A1 Mar. 13, 2003

(51) Int. Cl.[7] .................................................. A61B 18/14
(52) U.S. Cl. ........................ 606/37; 606/39; 606/40; 606/42
(58) Field of Search ........................ 606/34, 37–42, 606/45, 48–50

(56) References Cited

U.S. PATENT DOCUMENTS

| | | | | | |
|---|---|---|---|---|---|
| 4,123,673 A | * | 10/1978 | Gonser | ........................ | 606/42 |
| 4,188,927 A | * | 2/1980 | Harris | .......................... | 606/38 |
| 4,334,539 A | * | 6/1982 | Childs et al. | .................. | 606/37 |
| 4,463,759 A | * | 8/1984 | Garito et al. | .................. | 606/42 |
| 4,827,927 A | * | 5/1989 | Newton | ........................ | 606/37 |
| 5,067,953 A | * | 11/1991 | Feucht | .......................... | 606/34 |
| 5,342,356 A | * | 8/1994 | Ellman et al. | ................. | 606/32 |
| 5,954,686 A | * | 9/1999 | Garito et al. | .................. | 604/37 |
| 6,461,352 B2 | * | 10/2002 | Morgan et al. | ............... | 606/34 |

* cited by examiner

*Primary Examiner*—Lee Cohen

(57) ABSTRACT

An intelligent selection system for operating an electrosurgical instrument for use by a surgeon that depends primarily on the surgical procedure to be employed. The operating mode as well as other operating parameters can be controlled by the handpiece chosen by the surgeon to perform the procedure. Each handpiece is customized to activate when operated one of several preset operating modes of the electrosurgical instrument.

14 Claims, 9 Drawing Sheets

INTELLIGENT SELECTION SYSTEM FOR ELECTROSURGICAL INSTRUMENT

This invention is based on a Disclosure Document filed in the U.S. Patent And Trademark office on Jun. 6, 2001 and entitled INTELLIGENT SELECTION SYSTEM FOR ELECTROSURGICAL INSTRUMENT.

The invention is directed to an electrosurgical instrument, and in particular to an intelligent selection system and a handpiece for use in such a system for controlling an electrosurgical instrument or apparatus.

BACKGROUND OF INVENTION

Electrosurgical instruments are well known and widely used in the medical, dental, and veterinarian fields. They offer the capability of precision cutting and coagulation with electrosurgical currents preferably in the megacycle range using a handpiece with, for example, needle, ball, or loop electrodes in a unipolar operating mode or with a forceps in a bipolar operating mode. Ellman International, Inc. makes available an electrosurgical instrument for Radiosurgery which provides on its front panel connectors for receiving the plug of a cable-connected unipolar handpiece and a ground or indifferent plate, as well as connectors for receiving the plug of a cable-connected bipolar electrode. One form of such an instrument is described in U.S. Pat. No. 5,954,686, whose contents are incorporated herein by reference. Such instruments are characterized by different modes and sub-modes of operation. For example, the instrument described in the patent, which is typical of other similar instruments, has a cutting mode, separable into CUT and CUT/COAG sub-modes, and a coagulation mode, separable into HEMO, FULGURATE, and BIPOLAR sub-modes.

In a typical surgical setting using such an instrument, a surgeon may first use a handpiece while the instrument is in its cutting mode to perform a desired cutting procedure and then desire to use the same handpiece for coagulation of blood vessels while the instrument is in its coagulation mode. To this end, the electrosurgical instrument has on its front panel push buttons or switches for activating internal circuitry for switching the electrosurgical instrument from its cutting to its coagulation mode or vice-versa. A current electrosurgical instrument contains a power-supply-controlled radio-frequency (RF) oscillator which generates RF currents typically in the megacycle range as high-frequency AC waves. For most cutting purposes, the AC waveform is fully filtered to produce an approximate DC waveform. For most coagulation purposes, the AC waveform is partially rectified (commonly half-wave rectification) to produce the characteristic half-wave rectified waveform. This is accomplished by switching in certain rectifier and filter components for the cutting mode, and switching in certain rectifier components for the coagulation mode. This is well known in the art and further description is unnecessary. Suffice to say, the switching action occurs inside the instrument when the front panel controls are activated by the surgeon.

To simplify mode selection by the surgeon, it is known to place on the handpiece two finger-activated switches that can be connected by appropriate wiring to the electrosurgical instrument and wired in parallel with the front panel switches so that activation of either the finger switches on the handpiece or the front panel switches will allow mode selection. This is similar to the connection and operation of a foot switch that can be used by the surgeon to activate and deactivate the RF currents. More modern electrosurgical instruments, however, do not lend themselves to such a simple approach. The typical modern electrosurgical instrument is computer-controlled, typically by a microcontroller ($\mu C$); hence simple parallel-connected circuitry may not work satisfactorily. Another problem is that the standard handpiece has only three terminals, one of which is dedicated to carrying the high-frequency or RF electrosurgical currents; hence, mode selection must be carried out in a safe manner using only two of the three terminals.

A further complication in the use of such instruments is the variety of surgical procedures to which the instrument can be applied, often with different electrodes. Each surgical procedure typically requires not only a particular electrosurgical mode, such as cut or cut/coag, or hemo, but also may require a different set of mode conditions, such as the power setting and/or a different time duration of power application.

With four therapeutic waveforms available in current Radiosurgery instruments and a wide power range, it is time consuming and memory dependent on the part of the surgeon and or staff to tune in the correct waveform and power settings for the particular procedure to be carried out. Also there may have been occasions when electrosurgical injuries may have occurred due to incorrect waveform settings and incorrect power settings for the chosen procedure.

SUMMARY OF INVENTION

The principal object of the invention is an intelligent selection system for an electrosurgical instrument for use by the surgeon that depends primarily on the surgical procedure to be employed.

Another object of the invention is an intelligent selection system for use by the surgeon that depends primarily on the surgical procedure to be employed and can be controlled by the handpiece chosen by the surgeon to perform the procedure.

A further object of the invention is a handpiece-controlled electrosurgical instrument in which the choice of the handpiece controls the operating mode of the instrument and, preferably, also the mode conditions, such as the power setting that is desired for carrying out that particular procedure.

These objects are achieved in accordance with one aspect of the invention by a novel what may be termed intelligent electrosurgical system that incorporates multiple sets of stored or preset operating modes and conditions that allows the surgeon to select a particular set customized for the particular procedure to be carried out. So, for example, if procedure A is to be carried out, then set A is automatically selected, set A prescribing the electrosurgical mode of operation and one or more of the mode conditions specific to the selected procedure. Similarly, if procedure B is to be carried out, then set B is automatically selected, set B prescribing the electrosurgical mode of operation and one or more of the mode conditions specific to the selected procedure.

In principle, the selection system can be implemented by operating a multiple-position switch or switches on the front panel of the instrument, each switch or switch position being associated with one of the stored sets of operating modes and conditions. However, in accordance with a preferred feature of the invention, the selection is incorporated into the handpiece chosen by the surgeon. While it is possible to build into the handpiece a fingerswitch for each of the stored sets of modes, this has the disadvantage that if the surgeon presses the wrong fingerswitch, then the wrong operating mode for the current procedure may be inadvertently selected. It is therefore preferred in accordance with another feature of the invention to provide a family of intelligent or smart handpieces, each dedicated to a particular procedure.

In this preferred embodiment of the invention, each dedicated handpiece has incorporated in it means for generating a unique control signal that when processed by a computer in the electrosurgical instrument will automatically select that particular set of mode conditions specific to the procedure to which the handpiece is dedicated. There a number of different ways in which this feature can be implemented and the description that follows will describe several of the ways.

It is also possible to go to the next step and control the appearance of the handpiece, for example, by color-coding or by its shape, so that the surgeon understands that a specific colored or shaped handpiece is associated with a specific procedure, which will further minimize the possibility of surgeon error.

As a further feature of the invention, instead of providing handpieces which can typically receive one of several interchangeable electrodes, the electrode appropriate for the specific procedure can be molded into or otherwise fixed to the intelligent handpiece and made a permanent integral part of the handpiece, further minimizing the possibility of the surgeon choosing the wrong electrode for the specific procedure.

In a preferred embodiment, a handpiece construction is similar to the standard two-fingerswitch, three-terminal handpiece used heretofore except that means are included in the handpiece such that, when a first fingerswitch is activated, a first current level signal is outputted and when a second fingerswitch is activated, a second current level signal is outputted, both preferably from the same terminals. The means are chosen such that a $\mu$C in the instrument can distinguish the two current levels and activate the appropriate operating mode, for example, a cut mode for that particular procedure or a hemo mode for that particular procedure.

In another preferred embodiment, a handpiece construction incorporates memory means, preferably, a non-volatile memory clip, that stores information representing a set of mode conditions which when transmitted to the electrosurgical instrument automatically selects for the instrument that particular set of instrument mode conditions specific to the procedure to which the handpiece is dedicated.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described the preferred embodiments of the invention, like reference numerals or letters signifying the same or similar components.

DETAILED DESCRIPTION OF PREFERRED EMBODIMENTS

Figure 1:
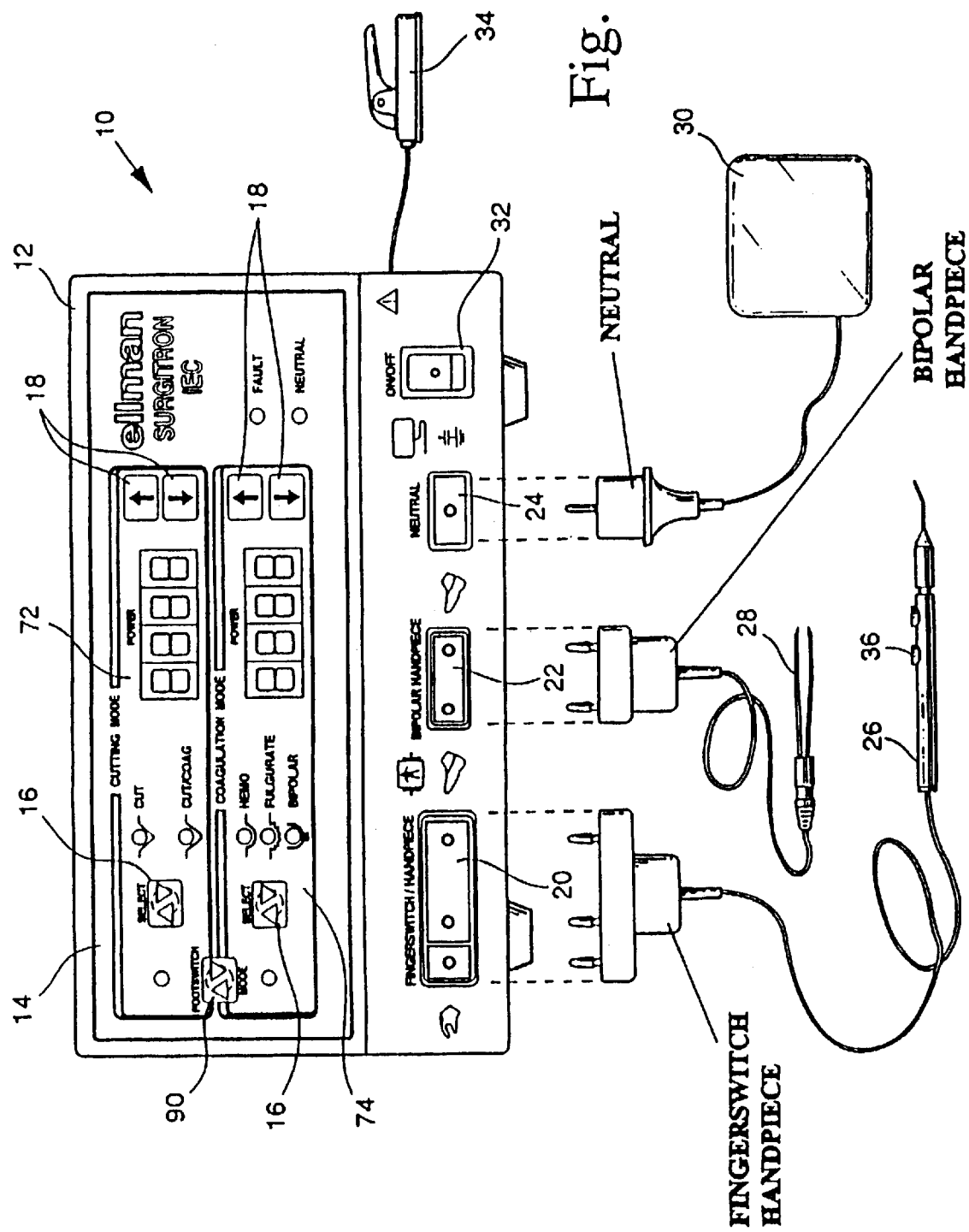
FIG. 1 is a schematic view of one form of electrosurgical instrument in accordance with the invention.

One form of an electrosurgical instrument 10 according to the invention is illustrated in FIG. 1. It comprises a system unit 12 having a box-like housing comprising at the front a control panel 14 for the instrument. The control panel includes touch switches 90 for selecting cutting or coagulation modes and touch switches 18 for controlling the power output by increasing or decreasing in steps the power, as indicated by upper and lower digital displays showing all 8's. At the bottom are output female connectors 20, 22, 24 for plugging in, respectively, at the left, a fingerswitch-controlled unipolar handpiece 26; at the center, a bipolar handpiece or forceps 28; and at the right a single or split neutral plate 30. An on-off power switch 32 is at the far right. The circuitry used to provide a fingerswitch-controlled unipolar handpiece may be of the type described in connection with the control unit 50 of U.S. Pat. No. 4,463,759, whose contents are herein incorporated by reference, which circuitry is in this case incorporated in the console unit 12. A connector (not shown) is provided at the side for receiving a conventional footswitch 34. Both the unipolar and bipolar handpieces can be simultaneously connected to the system unit 12 and operated in any order without touching the system unit or the control panel when the control panel has been preset or activated at the desired powers by each of the handpieces. For example, if the surgeon determines that s/he is going to perform a cutting procedure with a particular electrode, then s/he can set the cutting mode power on the upper digital display to, say, 80 watts by the up/down buttons 18. (Typically, these units are designed to supply up to 100 watts of RF power to either handpiece.) For coagulation with the bipolar handpiece, s/he may desire to use, say, 50 watts, which can also be set on the lower digital display by the up/down buttons 18. In this first embodiment, the internal circuitry is controlled in a known manner so that, when the fingerswitch unipolar handpiece is used, then RF power can be supplied to the electrode in the unipolar handpiece when a fingerswitch 36 on the handpiece 26 is depressed. However, when it is desired to use the bipolar handpiece 28, then the footswitch 34 is depressed, which then supplies RF power to the forceps of the bipolar handpiece. This result is a consequence of software control such that, while the machine mode is selected such that the fingerswitches on the unipolar handpiece can be used to apply power to the electrode (footswitch mode non-selected), only the footswitch can be used to apply power to the bipolar handpiece. This prevents power selected for the unipolar handpiece to be applied to the bipolar handpiece, and vice-versa. On the other hand, when it is not intended to use the bipolar handpiece and the footswitch mode is selected, then the footswitch can be used to operate the unipolar handpiece.

Figure 2:
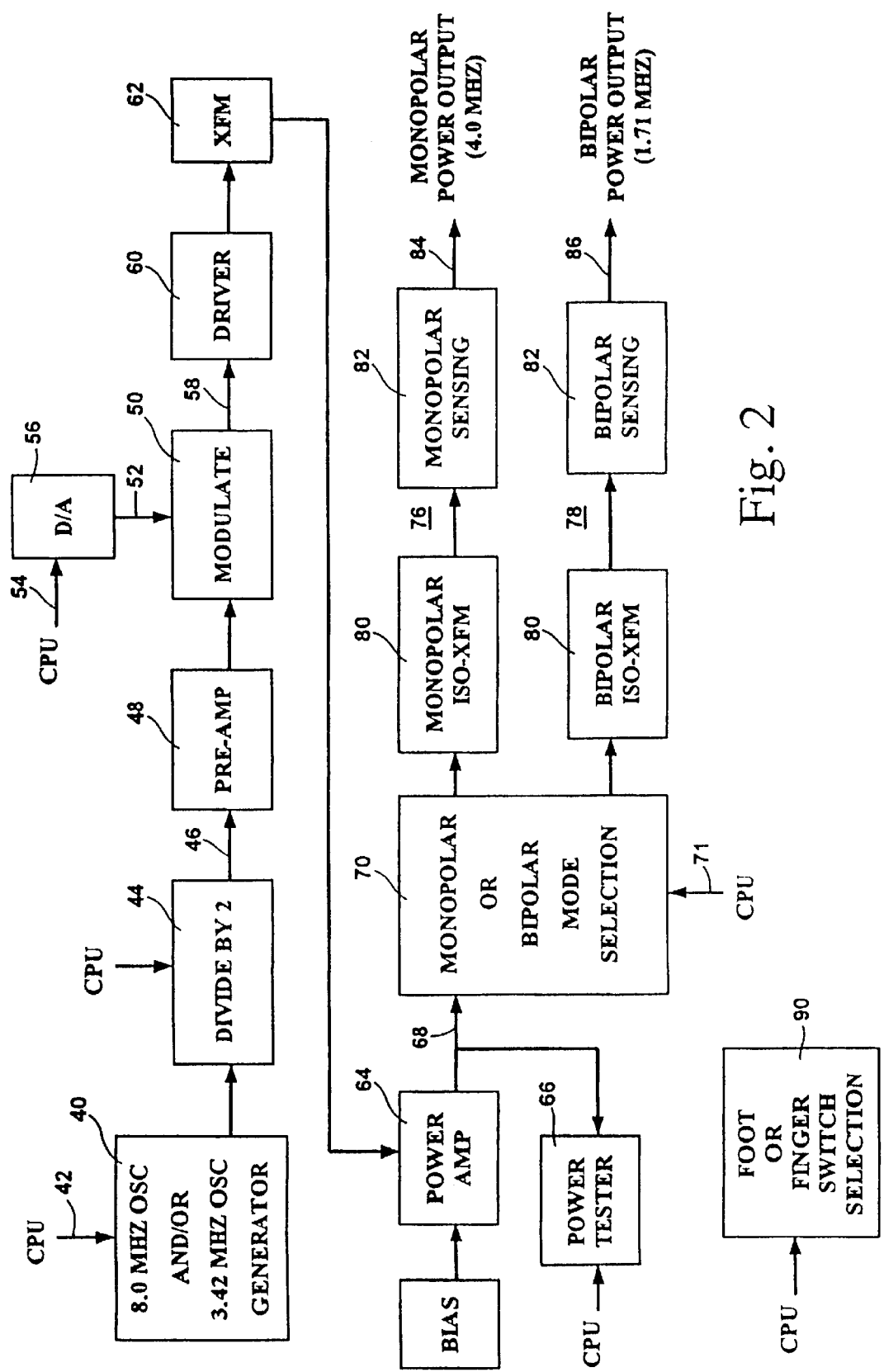
FIG. 2 is a circuit block diagram of one form of system circuitry for the electrosurgical instrument of FIG. 1.

One form of the RF circuitry to achieve the foregoing operation is illustrated in the block diagram of FIG. 2. The block 40 in the upper left contains two independent conventional RF oscillators generating, preferably, RF oscillations at 8.0 and 3.42 MHz respectively. As will be explained in greater detail below, the arrow 42 labelled CPU represents a selection signal generated by a conventional microcontroller under software control and inputted into the block 40 to select for operation either the 8.0 MHz oscillator or the 3.42 MHz oscillator. Both oscillators are constantly on when the power switch is activated, and the CPU selection 42 determines which of the third or fourth frequencies are outputted to the divide-by-2 block 44, resulting in an RF carrier 46 at either the first (4.0 MHz) or the second (1.71 MHz) frequency. That carrier is then pre-amplified in block 48 and inputted to a conventional modulator stage 50. Also input to the modulator stage is a modulating signal 52 derived from a CPU selection signal 54 and a D/A converter 56. The modulations referred to are the different output waveforms used for the known CUT, CUT/COAG, HEMO, and FULGURATE modes. These typically are: CUT-CW (full-wave rectified and filtered) output with maximum average power; CUT/COAG-full-wave rectified but unfiltered, deeply modulated, at 37.5 or 75 Hz rate, envelope with approximately 70% average to peak power ratio; HEMO-half-wave rectified and unfiltered, deeply modulated, at 37.5 or 75 Hz rate, envelope with approximately 35% average to peak power ratio; FULGURATE (or Spark-Gap Wave)-deeply modulated, 3.6 KPPS random rate with approximately 20% average to peak power ratio. Selection of the bipolar mode will automatically select the HEMO mode.

The RF power generating circuitry may be of the well known tube-type described in U.S. Pat. No. 3,730,188, whose contents are herein incorporated by reference, which is capable of generating a fully-rectified, filtered RF current for cutting, a full-wave rectified current for combining cutting and coagulation, and a half-wave rectified current for coagulation. Alternatively, the RF power generating circuitry can be of the well-known solid-state type capable of generating the same kinds of waveforms. The RF circuitry, as such, is not part of the present invention, as such circuits are well-known in the prior art. In this case, the RF circuitry provides two different frequencies of operation, a first high frequency in the range of 3.8–4.0 MHz, and a second high frequency in the range of 1.7–2.0 MHz, which is easily obtained by providing a known RF generator that provides a first and second outputs at the first and second higher frequencies and providing a simple known divide-by-two circuit for obtaining a second output at one half of the first or second frequency. Both outputs can be separately amplified and processed and made available at the console's output connectors depending on the switches activated. The present invention is not limited to the dual-frequency output operation.

After the modulated carrier has been generated at 58, it is processed through a standard driver 60, a transformer 62, and a power amplifier 64 controlled by a bias signal and whose input is monitored for safety's sake by a power tester circuit 66 under control of the CPU. The power amplifier output 68 is inputted to a mode selection block 70 under control of a signal from the CPU. The mode selection is made by the user by activating the upper panel 72 by pressing switch 16 in the upper panel, or the lower panel 74 by pressing switch 16 in the lower panel. That selection, made in conjunction with the selection 42, directs the output RF energy along the upper branch 76 or the lower branch 78. Both branches contain an isolation transformer 80 and a sensor 82 for operating indicators and preventing both branches from being activated at the same time. In other words, when the monopolar sensor 82 senses RF energy, the bipolar branch is disabled, and when the bipolar sensor 82 senses RF energy, the monopolar branch is disabled. The outputs 84, 86 shown at the right are directed to the connectors 20 and 22, respectively.

In this embodiment, the instrument is software controlled with the user supplying the switch inputs. One form of software control is illustrated by the flow chart depicted in FIG. 3. When the on-off switch 32 is toggled on, the microcontroller (not shown) is placed in its standby condition represented by block 88. The first action by the user is to select cutting mode or coagulation mode by pressing the switch 90 on the front panel, then pressing the upper or lower select switch 16 which determines which of the cutting or coagulation modes will be operable. If the coagulation mode is selected, the lower select switch 16 is used to select unipolar (HEMO or FULGURATE) or bipolar mode. The fingerswitch handpiece 26 operates exclusively of and independent from the footswitch mode selection 90 for all unipolar modes. This ensures that RF currents are available exclusively and at all times at one of the sockets 20, 22. If no such user action has occurred, tested at block 92, the CPU returns 94 to its standby condition. If a selection has been made 96, control is passed to the test block 98, which tests whether lower switch 16 has selected the bipolar mode. If yes 100, the circuitry to generate the 1.7 MHz carrier is selected at block 102, and control passes to the test block 104 which tests whether the footswitch 34 has been pressed, which is the only way by which 1.7 MHz currents can be made available at the bipolar handpiece socket 22. If no, the CPU returns 106 to its standby mode; if yes 107, RF energy is supplied to the bipolar handpiece socket 22.

If the bipolar mode was not selected at test block 98, then the circuitry to generate the 4.0 MHz carrier is selected at block 108, and control passes to a series of test blocks 110, 112, 114 which test, respectively, whether the CUT, HEMO, or FULGURATE modes have been selected by the user by means of upper and lower switches 16, which then provide the RF energy at 4.0 MHz at the monopolar connector output 20. If also the footswitch 34 was pressed, then the footswitch 34 can control when the RF energy is supplied to the handpiece 26; otherwise, the fingerswitch 26 on the unipolar handpiece 26 controls the delivery of RF energy to the patient.

In this operation using the instrument front panel switches, the ground plate 30 is always attached to the patient, and the surgeon can perform any desired unipolar or bipolar electrosurgical procedure. When both the unipolar and bipolar handpieces are plugged into the instrument console 12, then the desired operating conditions for each can be preset as desired. Then whichever handpiece is picked up and operated by the surgeon will automatically determine which is supplied with the appropriate RF currents. Thus, if the bipolar handpiece is selected and the footswitch activated, the bipolar handpiece will be supplied with 1.7 Mhz currents at the power setting manually selected by the user. On the other hand, if the unipolar handpiece is selected and its fingerswitch 36 activated, the unipolar handpiece will be supplied with 4.0 MHz currents at the power setting manually selected by the user. This operates on a first-come, first-served basis, which thus allows the surgeon to use the CUT mode for cutting with the unipolar handpiece followed with the bipolar handpiece for closing off any bleeders exposed during the cutting.

What has so far been described is the manual way of operating the instrument with conventional handpieces. In accordance with the present invention, instead of or in addition to using the manual mode of operation, an automatic mode is incorporated that is determined by the procedure to be performed by the surgeon or by the handpiece selected by the surgeon for the procedure. Preferably, the desired mode is selected by plugging an intelligent handpiece into the instrument. One example of such a handpiece will now be described in connection with FIGS. 4–7.

In this example, the handpiece comprises a generally conventional handpiece 110, with certain changes added in accordance with the invention, explained below, connected to a 3-line connector or terminal 112 which in turn is connected by way of a multi-line cable 114 to a control system 116 in turn connected to or a part of, as is more common, a conventional electrosurgical instrument 118 of the type illustrated in FIG. 1. The electrosurgical instrument 118 comprises an RF generator with the usual circuits to generate current waveforms in the high-frequency megacycle range, for example, 1–4 MHz, and also includes various circuit components to control the shape of the waveforms for various operating modes, including the cutting and coagulation modes as above described. The selection can be made by means of push buttons or switches on the control panel of the instrument. In the more modern electrosurgical instruments, the control is usually exercised by way of a computer, usually a $\mu C$, with the controls determining which inputs of the $\mu C$ are activated, which controls which outputs of the $\mu C$ are enabled, in turn in one embodiment switching in or out of the power-supply-controlled RF circuit rectifying and filter components (not shown as well known in the art) for the different modes selected.

In this preferred embodiment, the handpiece 110 comprises a pencil-type housing 111 on which is provided two fingerswitches 120, 122 for mode selection. In addition, it contains a chuck or other holding device 124 for receiving the shank of a conventional removable electrosurgical electrode 126. The shank is typically of metal, as is the chuck, which is connected by an electrical conductor 130 to one of the terminals of the connector 112. The two fingerswitches 120, 122 are also connected to the other two of the three terminal on the connector 112.

Figure 5:
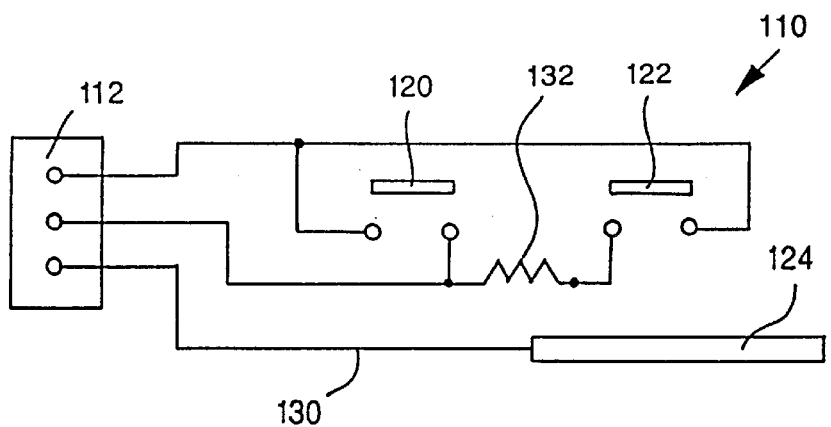
FIG. 5 is a circuit schematic of one form of electrical circuit for the handpiece of FIG. 4.

FIG. 5 shows the internal circuitry of the handpiece 110. The chuck 124 and line 130 carry the RF currents within the handpiece housing 111 to the electrode when inserted in the chuck 124. This uses the bottom terminal of the connector 112. The upper two terminals are connected inside of the housing 111 as shown to the two fingerswitches 120, 122. A resistor 132 is also mounted inside the housing 111. As will be observed, when switch 120 is closed, the circuit bypasses the resistor 132; however when instead switch 122 is closed, the circuit through the upper two terminal includes the resistor 132 in series.

Figure 6:
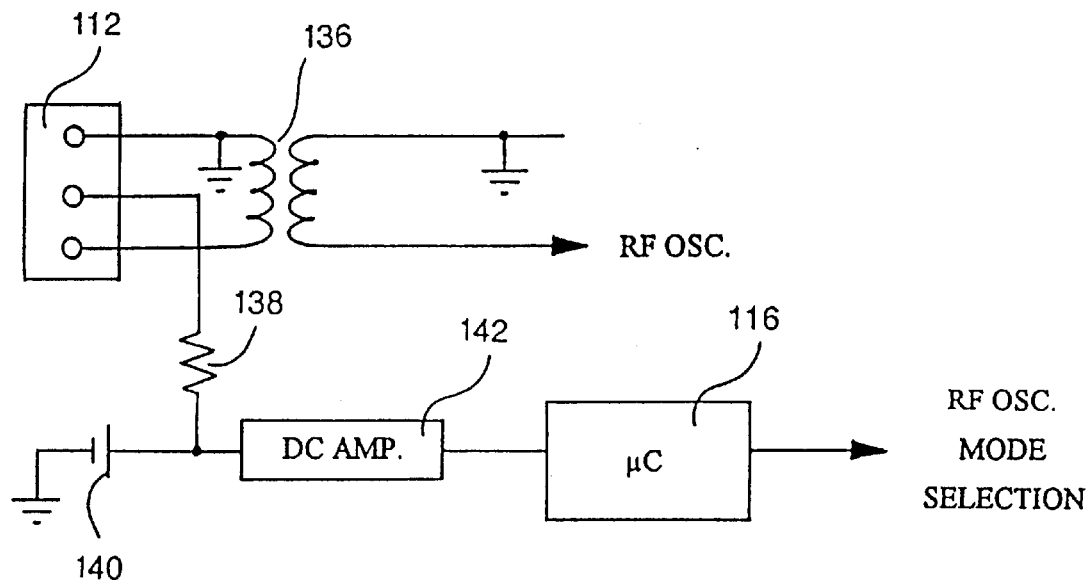
FIG. 6 illustrates schematically the interface connections in one embodiment between the handpiece of FIG. 4 and the electrosurgical instrument.

As schematically indicated in one embodiment illustrated in FIG. 6 for identifying the inputted control signal, the top terminal is grounded for safety's sake and together with the bottom terminal connected to an isolation transformer 136 which in turn is coupled to the RF oscillator. The center terminal is connected via a current limiting resistor 138 to a DC voltage source 140 which provides a DC current to a DC amplifier 142 whose magnitude is determined by which of the two fingerswitches are activated. When fingerswitch 120 is pressed, which bypasses the resistor 132, a higher level of DC current is fed to the amplifier 142. When fingerswitch 122 is pressed, which includes the resistor 132 in the circuit, a lower level of DC current is fed to the amplifier 142. The $\mu C$ is adjusted to distinguish between the two DC current levels and in a known way to activate one or more of its outputs which will select the desired operating mode that has been associated with the corresponding fingerswitch. Alternatively, the output from the amplifier 142 can be inputted to a DC comparator to which a reference current is supplied, with the comparator determining, as is well known, whether the input current is below or above the reference, with the comparator outputting, say, a "1" when the output current exceeds the reference or a "0" when the output current is below the reference. The $\mu C$ can then be set to respond to the digital "1" or "0" to select the operating mode.

In the preferred embodiment, the left fingerswitch 120 is used to select the cutting mode, and the right fingerswitch 122 is used to select the coagulation mode.

As will be observed, by the simple expedient of adding one or more small resistors 132 to the standard handpiece to change the DC current level established depending upon which of the two fingerswitches are activated, while continuing to use the standard three-terminal connector, it is possible to provide a simple DC output from two terminals which is easily interfaced to a standard $\mu C$ to control the operating mode of the electrosurgical instrument. The use of a DC circuit eliminates the possibility of noise or other interfering signal from the RF currents at the third terminal that can cause accidental mode switching.

Figure 7:
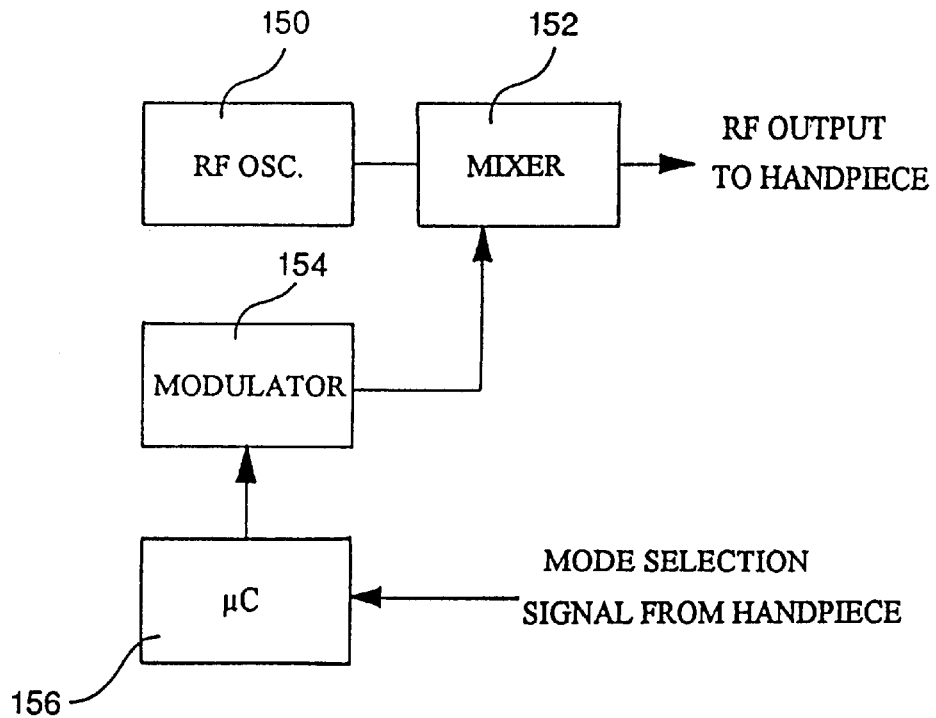
FIG. 7 illustrates schematically the circuit connections in another embodiment between the handpiece of FIG. 4 and the electrosurgical instrument.

FIG. 7 illustrates another preferred embodiment in which the cut and coag waveforms are generated in a somewhat different manner. In this embodiment, a conventional RF oscillator 150 generates a continuous wave (CW) output that is fed to a conventional mixer 152. The latter is controlled by a microcontroller 156. The microcontroller 156 in turn receives a low-level control signal or a high-level control signal from the handpiece 110 depending upon whether fingerswitch 120 or 122 is pressed. The microcontroller 156 may be software controlled, and in response to the handpiece signal input causes the modulator to produce no output or a signal at a 100–120 Hz rate which is ON for approximately one-half the cycle and OFF for the other half. The mixer 152 thus outputs, when no modulator signal is inputted, the unmodulated CW output for the cut mode; and when the described 100–120 Hz signal is inputted, the mixer outputs a deeply-modulated RF carrier envelope with an average to peak ratio of about 50% for the coag mode.

In this second embodiment, the output waveform is no longer dependent upon the power supply. An AC control current can be used in place of the DC current, at a voltage of about 5 volts at a frequency of about 300–500 KHz, which is below the megacycle range of the RF output to minimize interference.

In a further preferred embodiment of the invention, the current level controlling means is a simple impedance, preferably a resistor, mounted in the handpiece and connected to the two fingerswitches such that it is in or out of the circuit depending upon which fingerswitch is activated.

Besides low power and low cost, the fingerswitch mode controller of the invention is easily operable with relatively low frequency AC or direct currents (DC). This is important because the control circuitry that carries the two AC or DC levels of current is housed is the same pencil-type handpiece that includes the line carrying the RF AC currents which is a possible source of RF interference with such control systems for mode selection. For safety's sake it is important that no accidental undesired switching between the two modes occurs while a surgical procedure is being carried out. In addition, the system of the invention offers the advantages of accessibility and versatility, providing the surgeon all the benefits of fingerswitch selection of either electrosurgical mode.

The preferred embodiment uses a 100 ohm resistance for the mode selection resistor 132. With an AC current established at the upper two terminals of about 70 mA when the fingerswitch 120 is closed, when instead the fingerswitch 122 is closed, the introduction of the series resistor 132 reduces the DC current to about 3 mA. This difference is sufficient to be detected and when amplified or digitized can be used to control the $\mu$C. However, it will be apparent to those skilled in the art that the choice of resistance depends upon a number of factors including the type of $\mu$C used and the circuit components between the $\mu$C and the handpiece, and other resistance values would be appropriate with other circuits and is deemed within the scope of the invention. The benefit of the 100 ohm resistor is that, as a small wattage component, it is very small and easily fitted within the pencil-like structure of the housing 111, which typically has a diameter of about ½ inches or less, for example ⅜ inches, and a length of about 2¾ inches. Also, the invention is not limited to resistors as other small size impedances could be substituted capable of sufficiently changing the DC or AC current level upon activation of one or the other fingerswitch.

In the preferred mode of operation, the RF power is in a frequency range exceeding 1 MHz, 1.7–4 MHz being preferred. However, the invention is not so limited and other frequency ranges for electrosurgical procedures are also considered within the scope of the invention.

Figure 8:
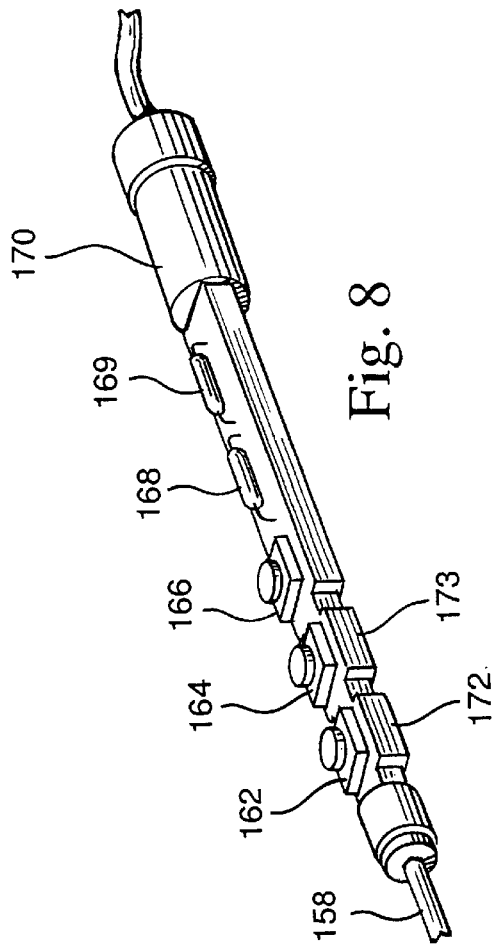
FIG. 8 is a partial perspective view of one form of 3-button handpiece according to the invention.
Figure 9:
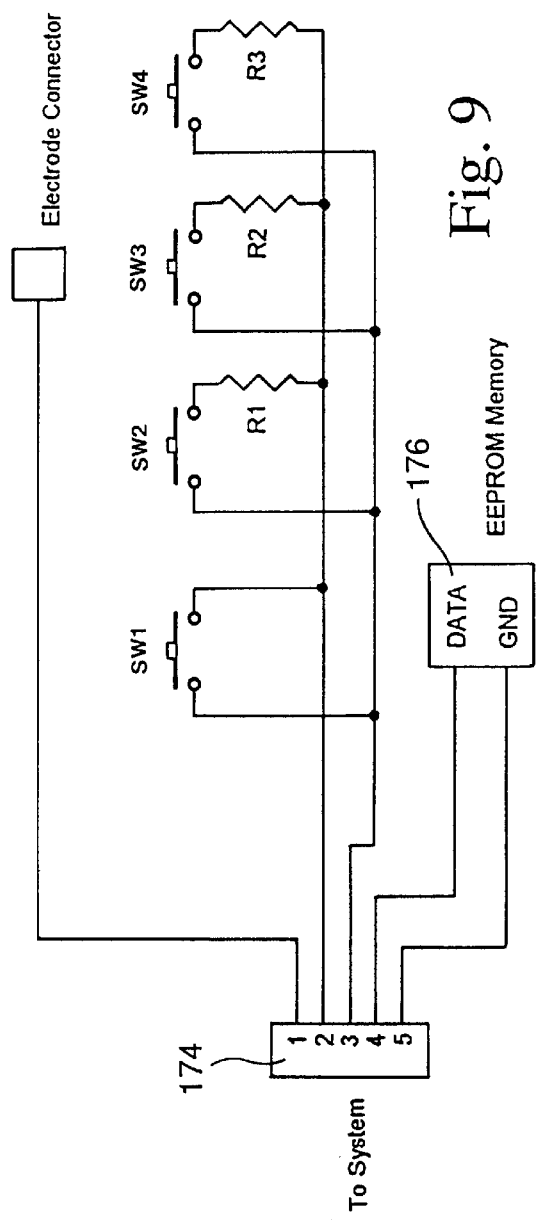
FIG. 9 is a circuit schematic of one form of 4-button handpiece according to the invention.

What has so far been described is how a novel construction of the handpiece can be used to generate a control signal to operate a $\mu$C which then controls the electrosurgical instrument to provide the correct mode of RF operating currents to the handpiece. It will be understood that the symbol for a microcomputer $\mu$C is also used herein to signify a microcontroller, commercial embodiments of which both contain for all practical purposes the same computing elements including a ROM to store a program in the usual way. In these embodiments, a first button of the handpiece is used to select unipolar operation and a second button is used to select bipolar operation. The invention is not limited to two-button handpieces but also includes handpieces with one or more additional buttons. FIG. 8 illustrates the internal construction of a handpiece provided with 3 buttons and 2 internal impedances and the standard 3-terminal output, and FIG. 9 is the schematic of a 4-button handpiece with 3 internal impedances, an internal non-volatile memory, e.g., an EEPROM, and a 5-terminal output. The FIG. 8 view is with the housing omitted to show one possible internal construction which comprises in front the electrode holder 158, three finger switches 162, 164, 166, two resistors 168, 169, and a cable holder 170 at the rear which terminates in a 3-terminal connector (not shown). PC boards 172, 173 can also be mounted below as shown if needed.

FIG. 9 illustrates one possible schematic for a 4-button handpiece SW1–SW4 with 3 impedances R1–R3 in the form of resistors. In this embodiment, a 5-terminal connector 174 is provided to increase the number of control signals that can be accommodated, as well as provide connections to an internal EEPROM 176 for reasons to be explained below. It is understood that the invention is not limited to separate connections for the finger switches and the EEPROM. As is well known in the $\mu$C used in watches, the same button or key can be used for different functions by having the $\mu$C sense multiple button presses, and associate for example function A with one key press and function B with two quick presses of the same key, and the same approach can be used in the invention but the illustrated arrangement is preferred.

Figure 10:
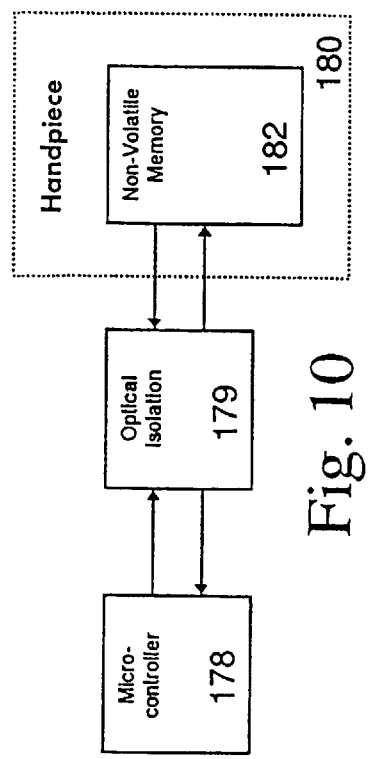
FIG. 10 is a block diagram showing how the handpiece of FIG. 9 can be interfaced to a microcontroller in the electrosurgical instrument.

A block diagram illustrating the interfacing arrangement of a $\mu$C to the handpiece is shown in FIG. 10. In this embodiment, the $\mu$C 178 is connected via conventional optical isolation 179 to the handpiece 180. The microcontroller 178 can communicate through a serial protocol to the EEPROM 182 (electrically erasable read only memory) incorporated inside the handpiece 180. Optical isolation is desirable to protect the processor 178 from RF noise generated while the instrument's output is active. The memory 182 in the handpiece can be read from and written to (if a read/write memory is used) by the processor 178 to allow the handpiece to store a variety of configuration and operational information.

Figure 11:
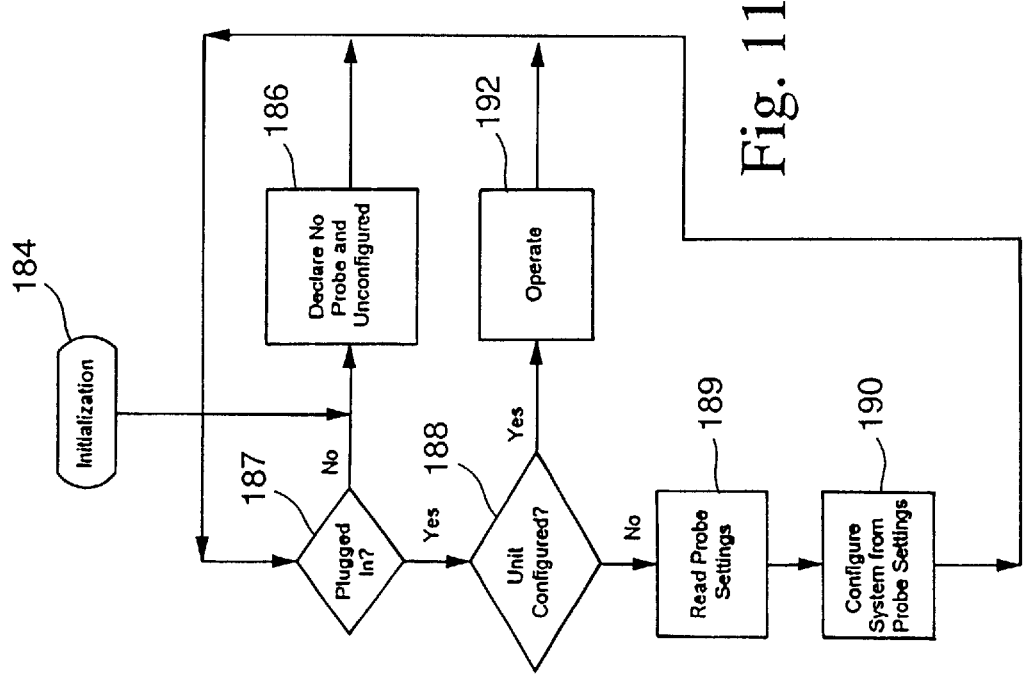
FIG. 11 is a flow chart indicating how the electrosurgical instrument can be programmed to operate with smart handpieces according to the invention.

A further example of how the selected mode, power, and time can be actually implemented in the instrument is illustrated by the flow chart in FIG. 11. Recall that the handpiece need not be limited to remembering or setting modes and power levels but must cooperate with the local electrosurgical instrument to provide the functions as described above. It will work with the Surgitron IEC II (Dual Frequency) electrosurgical instrument manufactured by the Ellman company but is obviously not limited to use with that particular system so long as the current system has been appropriately modified to include the necessary programmed $\mu$C to provide the functions as described. Some of those functions are illustrated in the flow chart of FIG. 11. The starting point is the initialization block 184. If no handpiece, sometimes referred to for brevity herein as "probe", has been connected to the instrument or it is unconfigured 186, the program branches to block 187 to check whether a probe has been connected. If the answer is no, the program loops back to block 187. If the answer is yes, the program falls through to block 188 to check whether the system is configured. If the answer is no, then, under control of the program, the system controller 178 accesses the internal EEPROM 182, reads 189 the EEPROM settings, and at block 190 then configures the instrument (system) to the correct mode and condition settings. The program then returns to block 187, proceeds then to block 188 and branches to the right to the block 192 which allows operation including if desired display of the operating parameters to the user based on the EEPROM settings.

In the read probe block 189, the $\mu$C receives an unambiguous indication of what buttons are physically on the probe and what modes they initiate. A probe could be configured to allow a unit to work only in one or certain modes, and could also be configured to allow the electrosurgical unit to put out only certain ranges of power in each allowed mode. In addition, the probe memory 182 could be used to implement the number of uses or elapsed time of use functions. A new probe might be set to 50 uses or 100 minutes of use to retain its reliability. When a probe has run out of time/uses it could be recharged (reprogrammed) or thrown away. The probe is typically factory-configured to define the above information. The instrument reads the probe data and configures itself. The hardware used to interface the handpiece to the instrument can be the same as that described in connection with FIGS. 1–7 above.

The mode and condition-setting functions can be incorporated in the probe or handpiece as just described or in the electrosurgical instrument or in both. In the case of the electrosurgical instrument, there are a number of different ways in which a handpiece key press or 2 key presses can select the mode and conditions of a particular procedure. The simplest way is to incorporate in the instrument a conventional look-up table that contains the mode and operating conditions for a number of different procedures, with the look-up table responding to a particular control signal (key) from the handpiece to vector to a subroutine which, equivalent to the surgeon's activation of the front panel switches, automatically switches the electrosurgical instrument to the correct mode and sub-mode and automatically sets the power to a specific value or to allow a specific range of values that will not harm the patient. A timer can also be included in the electrosurgical instrument so that the ON time of the instrument does not exceed a maximum time for the application of electrosurgical currents to the patient undergoing that procedure. As one example, a handpiece can be provided that is tailored for surgical procedures carried out with the instrument set at the cutting mode and the Cut or Cut/Coag sub-mode. The handpiece has incorporated in it a known blade electrode. For many cutting procedures, a typical power setting for tissue incisions is, say, 10 Watt, and a typical cutting duration rarely exceeds 10 sec. The handpiece tailored for cutting has a resistor of say 40 ohms connected to finger switch-2, and a resistor of say 30 ohms connected to finger switch-3. So, when finger switch-2 is pressed, a control signal of, say, 20 mA is sent to the instrument housing the $\mu$C and when finger switch-3 is pressed, a control signal of 30 mA is sent to the instrument housing the $\mu$C.

Figure 12:
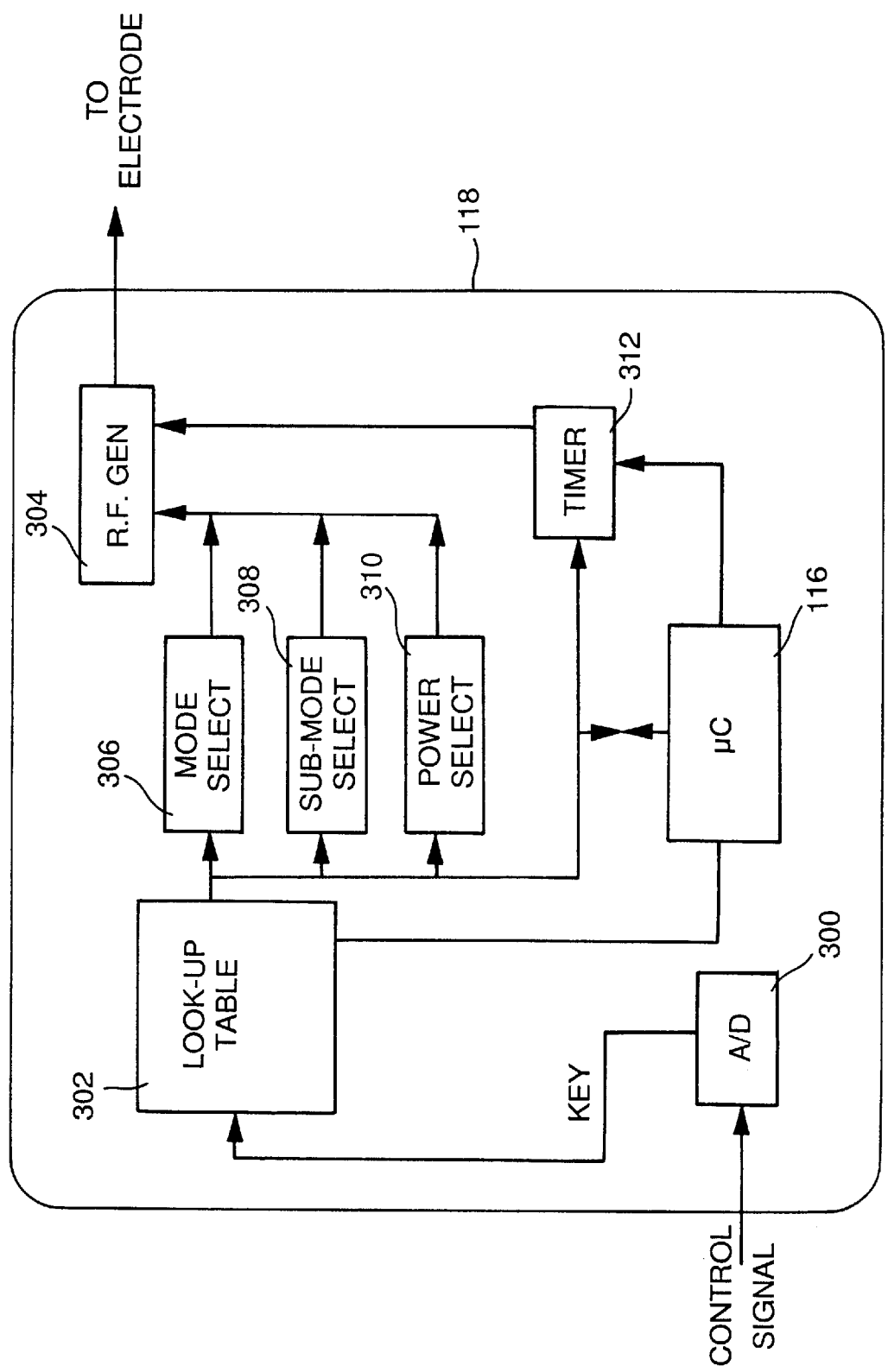
FIG. 12 shows a schematic block diagram of another embodiment of an electrosurgical instrument according to the invention.

Referring now to FIG. 12, which shows a schematic block diagram of an electrosurgical instrument according to the invention, inside the housing is a conventional analog-to-digital (A/D) converter 300 which converts the received control signals to a digital number representing a key to the look-up table. The digital number generated by the A/D converter when receiving a 20 mA signal and that generated when receiving a 30 mA signal are different and each corresponds to a different entry or key into the look-up table and thus a different subroutine is executed depending upon whether the control signal comes from the second or the third finger switch. The key outputted from the A/D converter is inputted to the look-up table 302 which, as illustrated below, could store three data items that are outputted to the RF generator 304 of the instrument. The first 306 is the mode-select signal which switches the RF generator to, say, the Cut mode. The second 308 is the sub-mode-select signal which switches the RF generator to, say, the Cut sub-mode. The third 310 is the power select signal which switches the RF generator to the desired power setting. In this particular case, assuming that finger switch-2 is associated with a Cut sub-mode at 10 Watt, then the outputs from the look-up table switch the instrument into the Cut sub-mode, and sets the power setting at 10 Watt, and, of course, in the usual way the activation of the finger switch causes the $\mu$C to execute the program illustrated in FIG. 3 resulting in the application of 4 MHz electrosurgical currents to the active electrode mounted at the end of the handpiece. A similar action takes place when finger switch-3 is pressed except that the different control signal when converted to a different digital number corresponds to a different entry or key into the look-up table resulting in switching of the instrument to the Cut/Coag sub-mode with a power setting of say 15 Watt. If desired, the look-up table can also incorporate a data item representing a duration not to exceed a fixed amount.

Figure 3:
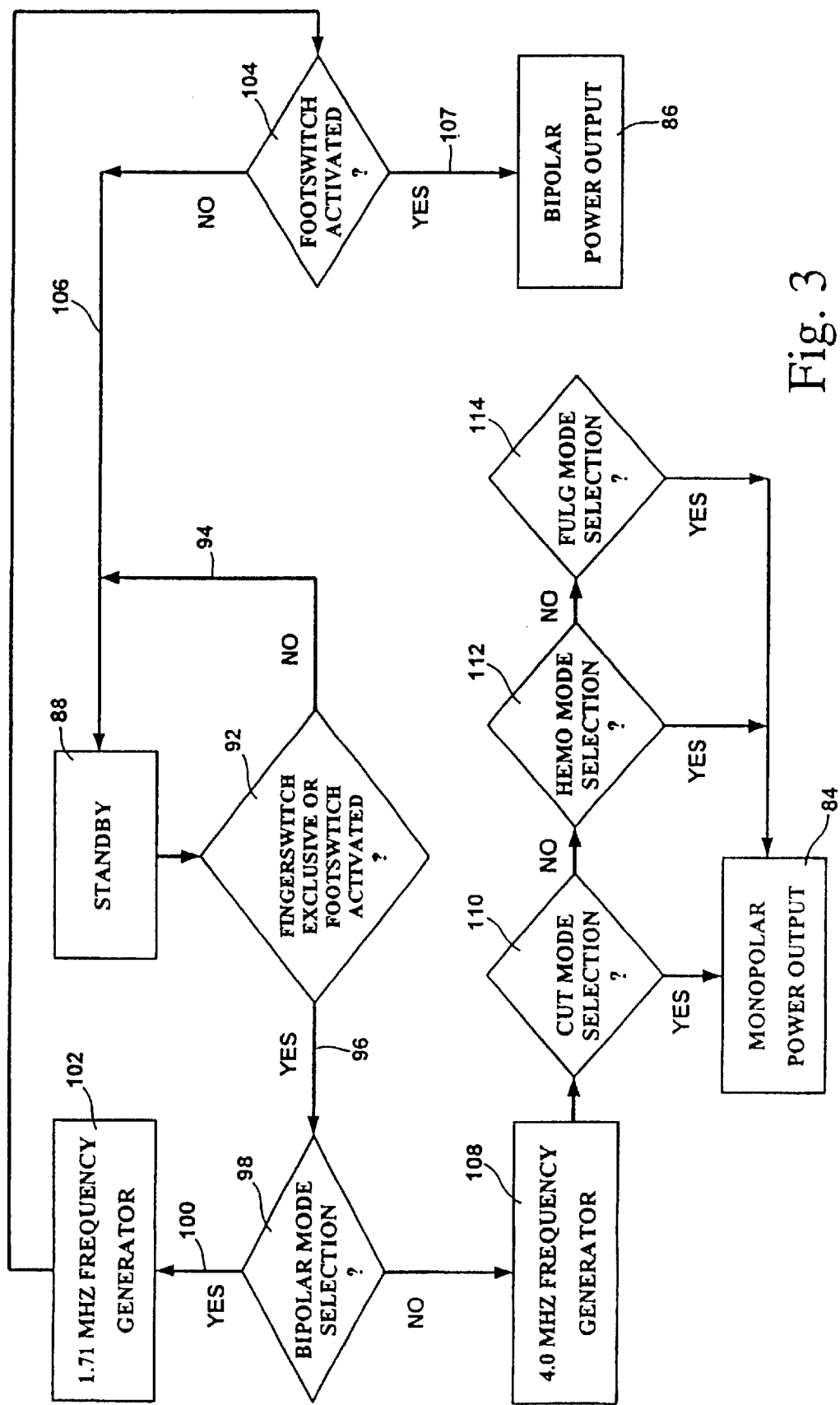
FIG. 3 is a flow chart illustrating how the system circuitry of FIG. 2 can be software controlled and operated in accordance with the invention.
Figure 4:
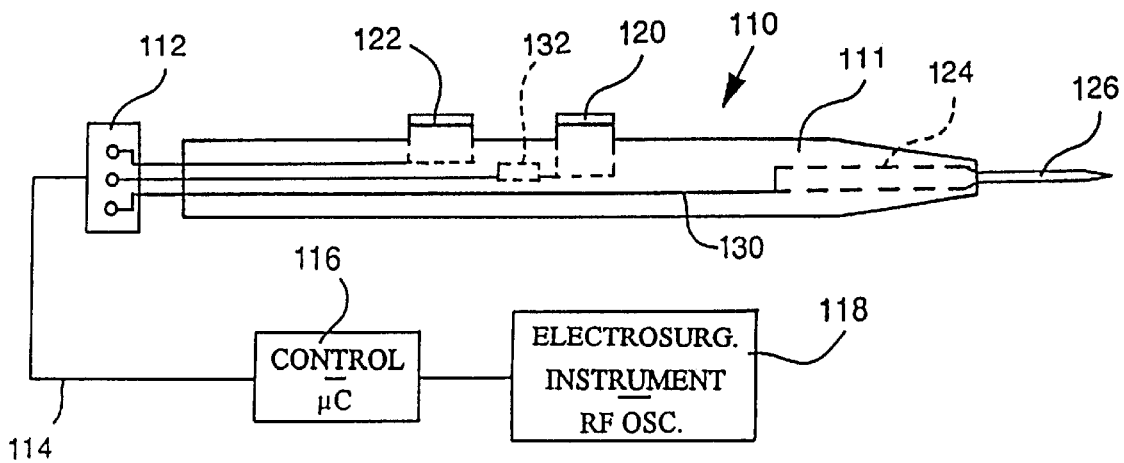
FIG. 4 is a schematic view showing a handpiece connected to an electrosurgical instrument in accordance with the invention.

The mode selection and power settings is a straight forward implementation using the principles and circuitry described in connection with FIGS. 1–3. The look-up table is an example of a database as a set of records each including an identifying key to uniquely identify the record and with each record in the set representing an operating condition of the instrument. In the relatively small database involved here, it can be implemented as an unordered list in which any record is easily accessed by inputting an identifying key which then outputs the record. The key here is the control signal generated by a particular key press or handpiece, converted to a digital number, and the record outputted could be, for example, a digital word the individual bits of which or combinations of bits represent a mode, sub-mode or mode condition (explained below). Alternatively, the database can be implemented as a table of records indexed by identifying keys, either as a 1-dimensional table or as a list of records. In either case, the inputted key produces a unique output record. The specific way of accomplishing outputting of records upon inputting of keys is not part of the present invention and is well known in the art.

Assuming the outputted record is a 16 bit word stored in a free register in the $\mu$C, then the $\mu$C can easily be programmed to access the bits to select specific modes and conditions. For example, the first bit can represent by a 0 the cutting mode and by a 1 the coagulation mode; the $2^{nd}$ and $3^{rd}$ bits can represent cut by 00 and cut/coag by 01 in the cutting mode, and in the coagulation mode 0 as hemo, 01 as fulgurate, and 10 as bipolar. The power setting can be represented by the $4^{th}$, $5^{th}$, $6^{th}$, $7^{th}$, and $8^{th}$ bits. Five bits can represent 32 different power settings. Assuming a power range of 1–64 watt, then 32 settings in that range separated by 2 watt intervals can be defined by the five bits. If finer divisions are required, 6 bits will define 64 different possible settings. Without a timer, then, even an 8 bit word will suffice. If timer settings are required, with finer power divisions, 7 bits of a 16 bit word will remain to define the duration settings which typically range from 1–50 sec. Similarly, by going to a 32 bit word, common in today's technology, then 16 bits will be available to select other conditions. Possibilities include: 1) in several procedures, it is common to irrigate the tissue cut or ablated. These additional bits can be used to turn on and off an irrigation pump supplying fluid to a tube mounted on the handpiece; and 2) it is also common to apply suction to the surgical site to remove undesirable plumes and odors. These additional bits can be used to turn on and off a vacuum pump supplying suction to a tube mounted on the handpiece.

In the latter embodiment, the database was incorporated inside the electrosurgical instrument, and the access keys supplied by the control signals inputted from the handpiece when specific keys are pressed. As a further alternative using two look-up tables, a non-volatile memory is provided in the handpiece (see FIG. 10) and stores in a lookup table in the memory 1–3 digital words which represents the desired electrosurgical modes and conditions. The $\mu$C in this case is located in the instrument. Assuming a 3-finger-button switch handpiece, 3 different control signals can be generated by the handpiece in response to pressing any one of the 3 buttons. When converted to a digital number, the handpiece control signal can act as an identifying key for a simple look-up table in the instrument, in which case the single output from the instrument look-up table is an identifying key for the handpiece lookup table. When the latter from the instrument look-up table is returned via a multiplexed data line to the handpiece look-up table, the handpiece look-up table will return on the same data line in a different time slot one of the 3 digital words stored in the handpiece look-up table. That returned word can be processed by the μC in the same manner as described above. In both of these embodiments, the handpiece becomes a dedicated or customized handpiece which generates a unique control signal from one or more of its buttons which represents instrument modes and conditions for one or more specific procedures, or generates a unique digital word when one or more of its buttons are pressed which also represents instrument modes and conditions for one or more specific procedures. In other words, the handpiece is factory-constructed or programmed to perform only certain procedures, and each surgical specialty will therefore require a family of several of these dedicated handpieces in order to perform several different procedures. This assures the surgeon that if he selects the right handpiece, then it is less likely that he will cause inadvertent injury to the patient. This can also be enhanced by color-coding or shaping the handpieces differently, so, for example, the blue colored or marked handpiece is specific to a cutting operation, and the red colored or marked handpiece is specific to a coagulation procedure.

In several of the previous embodiments, the dedicated handpiece comprises one or more buttons operating fingerswitches each of which represents a set of mode conditions which when transmitted to the electrosurgical instrument automatically selects for the instrument that particular set of instrument mode conditions specific to the procedure to which the handpiece is dedicated. However, it will also be understood in accordance with another feature of the invention that the dedicated handpiece does not require any buttons at all to be able to inform the electrosurgical instrument of the particular set of instrument mode conditions specific to the procedure to which the handpiece is dedicated. So, for example, by incorporating in the handpiece as illustrated in FIG. 9 memory means, preferably, a non-volatile memory chip, that stores one set of information representing instrument mode conditions specific to the procedure to which the handpiece is dedicated, then merely operating the instrument with that dedicated handpiece plugged in can easily be made to cause the handpiece to output a control signal representing the selected mode condition set for controlling the instrument which can be processed by the electrosurgical instrument in the same manner as described above. In this handpiece embodiment with no buttons, since only one procedure is possible, it is convenient to fix the electrode for that one procedure to the handpiece, as by molding it into the handpiece. This feature is also described and claimed in (a copending patent application, Ser. No. 09/962,025, filed Sep. 26, 2001, whose contents are herein incorporated by reference.

In the 4-button handpiece schematically illustrated in FIG. 9, the 4 buttons, SW1, SW2, SW3, SW4, are connected to a 5-pin connector 174 which can be plugged into a system with a matching connector, or to the system illustrated in FIG. 1 with an intervening adaptor and circuitry to allow three of the connector connections to be multiplexed to share the smaller number of connectors on the system panel. SW1 with no series resistor will produce a first control signal when pressed; SW2 with series resistor R1 will produce a second control signal when pressed; SW3 with series resistor R2 will produce a third control signal when pressed; and SW4 with series resistor R3 will produce a fourth control signal when pressed. These signals are outputted to terminal connections 2 and 3. The EEPROM 176 can be accessed via terminal connections 4 and 5 and conventional multiplexing. Terminal 1 is reserved for receiving and applying the selected RF electrosurgical currents from the system unit.

The table appearing below shows examples of how the control handpiece impedances can be arranged. In this case, each impedance is dedicated to a particular mode and a specific power level. For example, the impedance ZC00 is designated for the CUT mode with a power level of 100 Watts. By impedance in this context it will be understood is meant an incorporated element in the handpiece that causes the latter to output a particular control signal for this particular mode and output power setting. Thus, the incorporated impedance represents a corresponding pre-set function or electrosurgical procedure. A doctor may select the handpiece with the corresponding pre-set function that will serve the purpose of the desired procedure. The listed impedances and their designated modes and power levels are examples of how each impedance can be matched to its pre-set function.

TABLE

| Impedance No. | Waveform Mode | Waveform Sub-Mode | Power | Misc. (for other items if needed) |
|---|---|---|---|---|
| ZCOO | CUTTING | CUT | 50 | |
| ZBCO | CUTTING | CUT/COAG | 40 | |
| XNFO | COAGULATION | HEMO | 20 | |
| XSHO | COAGULATION | BIPOLAR | 10 | |

In this example, the letter Z can represent the CUTTING waveform mode; the letter X can represent the the COAGULATION waveform mode; the second letter the relevant sub-mode; the third and fourth letters various conditions such as power or duration. Sometimes the duration value in the record can represent a maximum value. This simply means that when that value is inserted in a countdown timer 312 (FIG. 12), the latter starts counting down when the RF electrosurgical currents are supplied to the handpiece electrode and will automatically shut down the electrosurgical currents when the timer reaches zero, as a safety feature. Of course, the physician can as usual stop the flow of currents by simply releasing the handpiece button whenever s/he desires.

In principle, the number of impedances has no limit. It can be as much as required to meet the desired pre-set functions. That is to say, the number of handpieces provided in a family equals the number of desired pre-set functions. Many kinds of surgical procedures require many kinds of different functions. Many kinds of different functions require many kinds of handpieces. The number of impedance that can be used will be chosen to match as many of the handpiece functions as desired. Each handpiece may have one or more buttons to activate the electrosurgical generator. The 3-button handpiece is one example of how a handpiece may control more than just one pre-set function. The smart electrode handpiece may have as many button switches as required to control the variety of pre-set functions by installing the corresponding impedances into the smart handpiece.

The output from the smart handpiece derived from the impedance is an analog voltage whose value is determined by the value of the impedance or sensor, which may be, for example, a resistor. The resistor analog voltage may be converted in a conventional A/D convertor to a digital number for the purposes taught above. However, the resistor is not a unique selection. The sensor can be any passive and/or active element, that includes resistor, inductor, capacitor, transistor, and even an integrated circuit.

The $\mu$C processes the received analog sensing signal/voltage through the A/D converter, and then matches the signal to a pre-set function. This can be done in the ways indicated above or in other ways. Besides the look-up table, a stored software program with a routine dedicated to that predetermined-set function in the $\mu$C is another preferred embodiment. When the program routine selected is executed, the $\mu$C can send out a digital signal to a digital-to-analog (D/A) converter to control an active circuit in the electrosurgical instrument to generate the specified waveform and its power level. One way of doing this has already been described above in connection with FIGS. 1–7. In summary, in this embodiment, the impedance in the smart electrode handpiece will output a control signal in the form of a different potential or voltage or current detected by a sensing circuit within the electrosurgical generator. The voltage is the electrical signal to inform the $\mu$C to fetch the pre-set function from ROM or in the software program, and then to execute the function. The receiving circuit in the instrument merely functions to read in the voltage or current change caused by the impedance and pass it on to the A/D converter for subsequent processing.

As described above, the table can be a look-up table stored in a ROM chip, or can be software routines in the $\mu$C. Each record or routine represents each impedance which corresponds to a specific pre-set function. However, the pre-set functions are not limited to the listed functions in the table. They can also include radio frequency applications, a temperature controller, timing duration, hertz stimulation, ultrasonic levels, amid other sorts of output signals.

It is preferred that the electrosurgical instrument contains "AUTO" and "MANUAL" modes. The electrosurgical instrument will select the pre-set function automatically when "AUTO" mode is selected. Otherwise, in "MANUAL" mode, the user gets the freedom to override the AUTO function and manually select a desired output waveform and its power level. Also, if the user desires, s/he may program the electrosurgical instrument to set or store this particular selection into the $\mu$C memory.

It is preferred that the selected function be confirmed to the physician after the selection has been made in the same way that happens upon MANUAL selection, namely, the instrument will display the pre-set function on the display panel to inform the user of its current mode and output setting.

Figure 13:
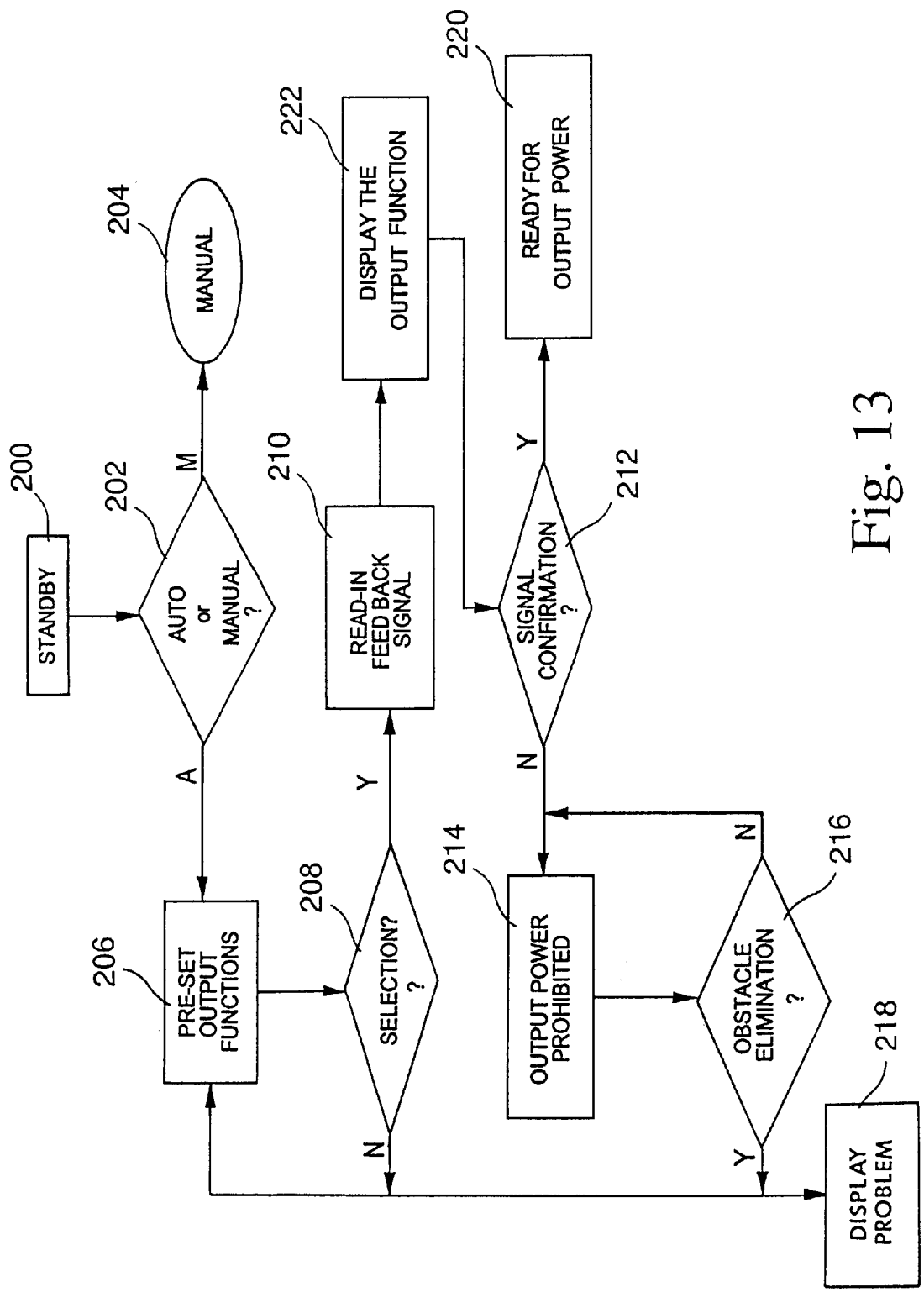
FIG. 13 is a flow chart illustrating one form of program for activating the MANUAL or AUTO mode of the instrument.

FIG. 13 is a block diagram illustrating one form of program for activating the MANUAL or AUTO mode of the instrument. The electrosurgical unit is at its initial state—standby mode 200—waiting for instruction from its terminal connector connected to the selected handpiece. The electrosurgical unit will sense from the control signal inputted by a handpiece button press whether AUTO or MANUAL has been selected. For example, one button of the handpiece can be dedicated to the MANUAL mode. Alternatively, if a look-up table is employed, one record selected can have only a single data item which tells the instrument that MANUAL mode has been selected. If it is MANUAL 202, then, the unit will adjust itself to the MANUAL mode 204 for further instructions from its front panel. If AUTO has been selected, the program takes the left branch to block 206 to process further inputs from the handpiece. If an improper selection 208 is made, the program returns to waiting block 206. When a selection has been made by a correct button press, the program branches to the routine 210 that reads the control signal and in block 212 compares the choices made against the values stored in the look-up table for validity. If, for example, too much power was indicated, the program branches to the left branch 214 and then to a routine 216 that attempts to make an appropriate adjustment. If this is impossible, the program returns to the waiting block 206 for another input. The improper input can be displayed to the user at block 218. If the signal is OK, the program takes the right branch which sets the correct instrument mode and sub-mode and prepares 220 to deliver the selected electrosurgical currents to the electrode attached to the handpiece. At the same time, the current modes and power setting can be displayed to the user via block 222.

The signal confirmation or validity check made at block 212 is present to control and enable the pre-set output power block 220. This is an important safety feature of this invention. Double-checking the pre-set output power ensures the quality and quantity of output power signal to be delivered for the procedure. This will reduce or prevent any problems from a component fault in the instrument or any uncertainty of the output power. If the confirming signal is not received, the output power port will disable the power output.

Several examples to illustrate how specific procedures determine the operating mode are as follows:

I. The procedure for treating telangiectasia (the light facial spider veins located on the facial, eye or nose areas.). The correct waveform for this procedure with the instrument described in the referenced patent is the partially rectified waveform, i.e., the Coagulation mode and Hemo submode. The preferred power setting is 1 or ½ watt. The preferred time is ¹⁄₂₀ of a second. The preferred electrode is a fine wire or needle.

II. Section Surgery—The correct waveform for this procedure with the instrument described in the referenced patent is the fully rectified waveform, i.e., the Cutting mode and Cut or Cut/Coag submode. The preferred power setting is about 10 watt. The preferred time is about 5 second. The preferred electrode is a blade or needle.

III. Epistaxis—The correct waveform for this procedure with the instrument described in the referenced patent is the partially rectified waveform, i.e., the Coagulation mode and Bipolar submode. The preferred power setting is about 35 watt. The preferred time is about 20 second. The preferred electrode is a bipolar forceps.

IV. Tonsillar Fulguration—The correct waveform for this procedure with the instrument described in the referenced patent is the spark gap type waveform, i.e., the Coagulation mode and Fulgurate submode. The preferred power setting is about 50 watt. The preferred time is about 1–2 second. The preferred electrode is a ball electrode.

Note that there are many more procedures than those used as illustrative above using electrosurgery, and the above examples were chosen merely to illustrate that each physician would have to remember the appropriate instrument settings as well as the appropriate electrodes and procedure duration times for each of these procedures or make labels to secure this operational information. If the wrong current or power and timing is used, it may result in burning of tissue, scarring, or excessive bleeding.

With the system of the invention using the intelligent handpiece and a proper insulated electrode, the physician simply plugs the handpiece into the instrument and goes immediately to the procedure with the confidence of precise, accurate waveform, power, and timing settings. A wide range of additional settings can, if desired, be added to those stored in the instrument.

Among the benefits of the invention are that it allows the handpiece or probe to be tissue and procedure specific. By choosing the correct handpiece, it is ensured that it will provide the precise waveform and power setting required by the chosen procedure. In addition, as another feature of the invention, the circuitry will allow the surgeon to override the settings determined by the handpiece by using the selective buttons on the instrument panel. If preferred, an extra fingerswitch button can be added to the handpiece to provide this override function.

Another advantage provided by the invention is that it enables the handpiece manufacturer to mold a procedure-specific electrode into the handpiece thus guaranteeing the correct electrode tip, with the handpiece dictating the waveform and power setting. In this case, the electrode is fixed to the handpiece and the handpiece can only be used with that electrode in the procedure determined by its incorporated sensor component.

It will also be understood that the invention is not limited to the specific connectors shown. Also, different shapes of the housing are also considered within the scope of the invention so long as the shape allows for easy hand holding by the surgeon and easy operation with his/her fingers of the two or more fingerswitches for mode selection. In the embodiments described, a control current is supplied to the handpiece and the control signal outputted depends upon the nature of the impedance in the pressed-button circuit. As an alternative, it is also possible to include a small battery, such as a watch battery, in the handpiece, the battery supplying the DC current to be modified by the impedance in the circuit to create the control signal.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. In combination:
a) an electrosurgical apparatus comprising a microcontroller and being capable of being switched via the microcontroller from a cutting mode to a coagulation mode and vice versa upon the inputting of mode selection signals to the microcontroller, said electrosurgical apparatus when in the cutting mode generating RF electrosurgical currents capable of performing a cutting operation when applied via an electrosurgical electrode and when in the coagulation mode generating RF electrosurgical currents capable of performing a coagulation operation when applied via the electrosurgical electrode,
b) a handpiece for connection to the electrosurgical apparatus and comprising fingerswitches for selectively providing cutting mode or coagulation mode electrosurgical currents from the electrosurgical apparatus to an electrode connected to the handpiece, said handpiece comprising:
(i) a housing,
ii) at least first and second fingerswitches on the housing,
iii) means on the housing for receiving and holding an electrode for delivering RF electrosurgical currents,
iv) means connected to the housing for supplying a control current to the fingerswitches,
v) means connecting the fingerswitches such that when the first fingerswitch is activated a first current level is established and when the second fingerswitch is activated a second current level is established,
c) said first and second current levels serving as the control signals and being usable by the microcontroller to select an operating mode of the electrosurgical apparatus,
d) further comprising a non-volatile memory in the handpiece and accessible from the microcontroller.

2. In combination:
a) an electrosurgical apparatus comprising a microcontroller and being capable of being switched via the microcontroller from a cutting mode to a coagulation mode and vice versa upon the inputting of mode selection signals to the microcontroller, said electrosurgical apparatus when in the cutting mode generating RF electrosurgical currents capable of performing a cutting operation when applied via an electrosurgical electrode and when in the coagulation mode generating RF electrosurgical currents capable of performing a coagulation operation when applied via the electrosurgical electrode,
b) a handpiece for connection to the electrosurgical apparatus and comprising fingerswitches for selectively providing cutting mode or coagulation mode electrosurgical currents from the electrosurgical apparatus to an electrode connected to the handpiece, said handpiece comprising:
i) a housing,
ii) at least first and second fingerswitches on the housing,
iii) means on the housing for receiving and holding an electrode for delivering RF electrosurgical currents,
iv) means connected to the housing for supplying a control current to the fingerswitches,
v) means connecting the fingerswitches such that when the first fingerswitch is activated a first current level is established and when the second fingerswitch is activated a second current level is established,
c) said first and second current levels serving as the control signals and being usable by the microcontroller to select an operating mode of the electrosurgical apparatus,
d) the means of claim element b)v) comprising a small impedance having a value of about 100 ohms.

3. An intelligent mode-selection system for an electrosurgical instrument comprising:
(a) an electrosurgical instrument capable of receiving a plurality of control signals for selecting an operating mode, each of said control signals when received by the electrosurgical instrument being capable of placing the instrument into one of a plurality of operating electrosurgical modes, each of the operating modes generating RF electrosurgical currents each characterized by a different RF waveform capable of one of cutting or coagulation of tissue when the RF electrosurgical currents are applied to a patient to carry out a specific procedure requiring a particular operating mode,
(b) a handpiece for connection to the instrument and comprising multiple fingerswitches and having an output,
(c) component means in the handpiece each connected to one of the fingerswitches for generating, when supplied with current and when a fingerswitch is activated, at the handpiece output one of a plurality of control signals, each of the control signals being associated with one of the plurality of operating electrosurgical modes for executing a particular procedure on the patient, (d) means on the handpiece for holding an electrode for delivering to the patient one of the plurality of RF electrosurgical currents each representative of one of the instrument's operating modes, (e) means for outputting the control signals to the electrosurgical instrument in response to the activation of the fingerswitches for selecting one of the operating modes, (f) means in said instrument in response to receipt of the control signals from the handpiece for supplying to the electrode RF electrosurgical currents in the selected mode having the characteristic waveform for performing the particular cutting or coagulation procedure.

4. An intelligent selection system for an electrosurgical instrument as claimed in claim 3, further comprising a microcontroller for controlling the instrument and a storage system in the electrosurgical instrument, said storage system being capable of storing preset information representative of each of the plurality of operating modes and in response to any one of the control signals outputting control information, said microcontroller in response to the control information controlling the instrument such that the instrument is placed in the operating mode associated with the activated fingerswitch.

5. An intelligent selection system for an electrosurgical instrument as claimed in claim 3, further comprising a microcontroller including routine stores for controlling the instrument in the electrosurgical instrument and software for controlling the microcontroller, said software being capable of executing prestored routines each representative of one of the plurality of operating modes and in response to any one of the control signals controlling the operation of the microcontroller such that that routine is executed that places the instrument in the operating mode associated with the activated fingerswitch.

6. An intelligent selection system for an electrosurgical instrument as claimed in claim 3, wherein each operating mode includes a selected one of a plurality of electrosurgical current output powers to the electrode.

7. An intelligent selection system for an electrosurgical instrument as claimed in claim 6 wherein each operating mode also includes a selected one of a plurality of time durations of electrosurgical currents to the electrode.

8. An intelligent selection system for an electrosurgical instrument as claimed in claim 3, further comprising at least one additional handpiece, each of the handpieces comprising an electrode integral with and fixed to the handpiece, each handpiece including means for generating a unique control signal, the electrode of each handpiece being customized for performing particular medical procedures associated with a specific one of the control signals, means in said instrument in response to receipt of the control signals from each of the handpieces for supplying to the integral electrode RF electrosurgical currents in a selected mode customized for the procedure for which the handpiece is customized.

9. An intelligent selection system according to claim 3, wherein the means of claim element (d) includes an electric connection to the electrode, further comprising an electrical connector comprising three terminals, one of which is connected to the electrode via the electric connection and the other two of which are connected to the fingerswitches.

10. An intelligent selection system according to claim 3, wherein the control signals are DC currents or AC currents at a lower frequency than that of the RF electrosurgical currents.

11. An intelligent selection system according to claim 10, wherein the component means comprises different small impedances.

12. In combination:
a) an electrosurgical apparatus comprising a microcontroller and being capable of being switched via the microcontroller from a cutting mode to a coagulation mode and vice versa upon the inputting of mode selection signals to the microcontroller, said electrosurgical apparatus when in the cutting mode generating RF electrosurgical current waveforms capable of performing a cutting operation when applied via an electrosurgical electrode to a patient and when in the coagulation mode generating different RF electrosurgical current waveforms capable of performing a coagulation operation when applied via the electrosurgical electrode to the patent,
b) at least one handpiece for connection to the electrosurgical apparatus and comprising mode-selection-signal-controlling means for selectively providing cutting mode or coagulation mode electrosurgical current waveforms from the electrosurgical apparatus to an electrode connected to the handpiece, said handpiece comprising:
  (i) a housing,
  (ii) means on the housing for receiving and holding an electrode for delivering RF electrosurgical currents to the patient,
  (iv) means connected to the handpiece housing for supplying a control current to the mode-selection-signal-controlling means, said mode-selection-signal-controlling means in response to the control current establishing a first or second current level,
c) said first and second current levels serving as the made selection signals and being usable by the microcontroller to select an operating cutting or coagulation mode of the electrosurgical apparatus associated with the first or second current levels.

13. The combination according to claim 12, wherein the electrosurgical apparatus comprises a database or look-up table connected to the microcontroller, each of the mode selection signals representing a key to one of plural records in the database or look-up table, each of the records representing an operating cutting or coagulation mode of the electrosurgical apparatus.

14. The combination according to claim 13, wherein the RF electrosurgical currents are in the megacycle range, and the current levels are an AC current in the kilocycle or lower range.

* * * * *